US006939551B2

United States Patent
Amato et al.

(10) Patent No.: US 6,939,551 B2
(45) Date of Patent: Sep. 6, 2005

(54) COSMETIC FILMS

(75) Inventors: Steven W. Amato, North Plainfield, NJ (US); Wayne M. Hoyte, Parlin, NJ (US); Alexander Naranjo, Mine Hill, NJ (US); Shirish Patel, Guttenberg, NJ (US); Salvatore Barone, Staten Island, NY (US)

(73) Assignee: Coty Inc., New York, NY (US)

( * ) Notice: Subject to any disclaimer, the term of this patent is extended or adjusted under 35 U.S.C. 154(b) by 208 days.

(21) Appl. No.: 10/152,314

(22) Filed: May 20, 2002

(65) Prior Publication Data

US 2003/0124154 A1 Jul. 3, 2003

Related U.S. Application Data

(60) Provisional application No. 60/292,424, filed on May 21, 2001.

(51) Int. Cl.⁷ .................................................. A61K 7/04
(52) U.S. Cl. .......................................... 424/401; 424/61
(58) Field of Search ................... 424/401, 61

(56) References Cited

U.S. PATENT DOCUMENTS

| | | | |
|---|---|---|---|
| 4,421,881 A | 12/1983 | Benkendorf et al. ......... 524/24 |
| 5,093,108 A | * 3/1992 | Pappas et al. ................. 424/61 |
| 5,227,155 A | 7/1993 | Castrogiovanni et al. ...... 424/61 |
| 5,275,807 A | 1/1994 | Pappas et al. ................. 424/61 |
| 5,290,543 A | 3/1994 | Ounanian et al. ............. 424/61 |
| 5,792,447 A | 8/1998 | Socci et al. ................... 424/61 |
| 5,882,636 A | 3/1999 | Mui et al. ..................... 424/61 |
| 6,126,952 A | 10/2000 | Socci et al. ................. 424/401 |

FOREIGN PATENT DOCUMENTS

WO    WO-02/058644    8/2002

OTHER PUBLICATIONS

"Pelemol Bip", Phoenomenon #110, Phoenix Chemical, Inc., 60 Fourth Street, Somerville, NJ 08876, (REV. Sep. 5, 2000, pp. 2).*

"Pelemol Bip", *Phoenomenon #110,* Phoenix Chemical, Inc., 60 Fourth Street, Somerville, NJ 08876, www.phoenix–chem.com,(REV. Sep. 5, 2000),pp. 2.

* cited by examiner

*Primary Examiner*—Thurman K. Page
*Assistant Examiner*—Sharon Howard
(74) *Attorney, Agent, or Firm*—Schwegman, Lundberg, Woessner & Kluth, P.A.

(57) ABSTRACT

The present invention includes a cosmetic film. The film includes butylphthalimide isopropylphthalimide, one or more primary film forming polymers and one or more secondary film forming resins.

12 Claims, No Drawings

COSMETIC FILMS

This application claims the benefit of Provisional application Ser. No. 60/292,424, filed May 21, 2001.

TECHNICAL FIELD

The present invention relates to compositions useful as cosmetic films formed from plasticizers alternative to replace phthalates. The compositions herein are particularly useful as coatings for mammalian nails, and are useful as basecoat, topcoat and colored nail polish compositions.

BACKGROUND OF THE INVENTION

Nail polish compositions have long been promoted as having long wear, good adhesion, and/or resistance to chipping. While some nail polish compositions have provided better wear than others, a need remains for nail polish compositions providing long wear and employing plasticizers other than phthalate compounds.

Nail polish has, over the decades, been developed to have multi-faceted functionality. In addition to having functionality, polish must be aesthetically pleasing when applied to fingernails and toenails in order to provide a desired color to the nails. The polish must also be resistant to chipping, cracking, splintering and peeling when subjected to a wide range of environments. Over the years, nail polishes have been developed which have these properties to varying degrees.

Nail polishes have typically included pigments and dyes that are suspended in a viscous matrix. The viscous matrix typically includes a film forming component and a plasticizer, namely dibutyl phthalate. The nail polish has also included an adhesion promoter, a polymeric component formed by the condensation polymerization of formaldehyde or other sulfonamide formaldehyde resin.

It has been observed over the years that phthalates and aldehyde condensation product exposure has been undesirable for some users because the users are sensitized to these materials. There has been an effort to replace the polymeric component with other materials that do not cause a sensitization. However, the replacement materials have produced a nail polish that is deficient in features such as high gloss, defined color, long wear, chip resistance, nail flexibility and adherence.

SUMMARY OF THE INVENTION

One embodiment of the present invention includes a cosmetic film. The film includes butylphthalimide isopropylphthalimide, one or more primary film forming polymers and one or more secondary film forming resins.

Another embodiment of the present invention includes a nail enamel. The clear nail enamel includes butylphthalimide isopropylphthalimide. The nail enamel also includes a secondary film-forming polymer, nitrocellulose and a polyester resin.

One other nail enamel embodiment of the present invention is a colored nail enamel, that includes butylphthalimide isopropylphthalimide in a concentration of about 1 to 10 percent by weight; ethyl acetate in a concentration of about 37 to 39 percent by weight; butyl acetate in a concentration of about 19 to 26 percent by weight; nitrocellulose in a concentration of about 11 to 14 percent by weight; isopropyl alcohol in a concentration of about 5 to 6 percent by weight; optionally, polyester resin in a concentration of about 10 to 12 percent by weight; optionally, tosylamide/epoxy resin in a concentration of about 8 to 10 percent by weight; stearalkonium hectorite in a concentration of about 0.5 to 2 percent by weight; acrylic copolymer in a concentration of about 1.5 percent by weight; and coloring agents in a concentration effective to produce color.

Another embodiment of the present invention includes a nail enamel that includes a plasticizer and butylphthalimide isopropylphthalimide (BIP) in a concentration effective for imparting to the nail enamel, adhesion, hardness and flexibility that is retained for at least about seven days, when the nail enamel is applied to a nail.

The present invention also includes a colored nail enamel, comprising: ethyl acetate; butyl acetate; nitrocellulose; isopropyl alcohol; tosylamide/epoxy resin; butylphthalimide isopropylphthalimide in a concentration of about 1 to about 10 percent by weight; and coloring agents.

The present invention also includes a method for making a cosmetic film that has a hardness, adhesion, and flexibility, gloss, and long shelf life, comprising:

providing one or more primary film forming polymers;

providing one or more secondary film forming resins;

providing butylphthalimide isopropylphthalimide;

and blending the primary film forming polymer, secondary film forming resin and butylphthalimide isopropylphthalimide (BIP), wherein the BIP has a weight percent concentration of about 1 to 10 weight percent to make a cosmetic film having a hardness, adhesion, flexibility, gloss and long shelf life.

Another embodiment of the present invention is a method for coating nails. The method includes providing a cosmetic film that includes butylphthalimide isopropylphthalimide and applying the cosmetic film to one or more mammalian nails.

One other embodiment includes a colored nail enamel. The colored nail enamel includes an acetate, nitrocellulose, butylphthalimide isopropylphthalimide, tosylamide/epoxy resin and coloring agents.

Other embodiments include cosmetic films that comprise butylphthalimide isopropylphthalimide; films that comprise butylphthalimide; and films that comprise isopropylphthalimide.

DETAILED DESCRIPTION

One embodiment of the present invention includes a nail enamel composition that comprises butylphthalimide isopropylphthalimide, BIP. The nail enamel of the present invention is, for some embodiments, free of phthalates and, for some embodiments, free of aldehyde condensation products. The nail enamel composition also includes one or more primary film forming polymers and one or more secondary film forming resins. The nail enamel compositions of the present invention include primary film forming polymers and combinations thereof in an amount ranging from about 5 to 20% by weight, and, for some embodiments, in the range of about 9 to 14% by weight.

In addition to the primary film forming polymer and secondary film forming resin, the nail enamel compositions according to the present invention also include at least one plasticizer to soften and to plasticize the primary film forming polymer. The plasticizer as well as combinations thereof, is in either liquid or solid form.

In its product aspect, embodiments of the present invention provide nail enamel compositions which are suitable for use as base coats, color coats, clear coats and protective top coats while maintaining the desirable characteristics of the nail enamel compositions. The nail enamel compositions display good lastingness and chip resistance, and are safe to use with frequent applications.

The present invention includes a use of butylphthalimide isopropylphthalimide, Pelemol BIP, as a plasticizer in nail enamel compositions. Hereinafter, Pelemol BIP is referred to as BIP. While Pelemol BIP is described herein, it is believed that butylphthalimide and isopropylphthalimide, when obtained separately, can be blended to obtain a plasticizer suitable for use in the nail enamel of the present invention. It is also believed that butylphthalimide and isopropylphthalimide are individually usable as plasticizers in nail enamel compositions.

As used herein, the term, "cosmetic film" refers to a nail enamel usable as a base coat, color coat, clear coat and protective top coat. As used herein, "lacquer," "polish" and "enamel" are used interchangeably.

Referred to herein are trade names for materials including, but not limited to, polymers and optional components. The inventors herein do not intend to be limited by materials described and referenced by a certain trade name. Equivalent materials (e.g., those obtained from a different source under a different name or catalog (reference) number) to those referenced by trade name may be substituted and utilized in the methods described and claimed herein. All percentages and ratios are calculated by weight unless otherwise indicated. All percentages are calculated based on the total composition unless otherwise indicated. All component or composition levels are in reference to the active level of that component or composition, and are exclusive of impurities, for example, residual solvents or by-products, which may be present in commercially available sources.

The cosmetic properties of the nail varnish of the present invention include good adhesion to the surface of the nail. In addition, the varnish film is homogeneous and glossy, and exhibits a degree of flexibility that prevents premature cracking and flaking off the nail. In order to obtain such properties, the varnish film is sufficiently soft. This softness allows the film to withstand impact and deformations of the matrix of the nail. However, the film retains an acceptable degree of gloss and is sufficiently hard to prevent scratches and cracks. Nail enamel embodiments are believed to be resistant to cracking for at least about ten days after application to a nail.

The film-forming polymers used in the lacquer of the present invention are selected from polyurethanes, polyacryls, polymethacryls, cellulosic polymers, styrene-acryl copolymers, polystyrene-polyacryl mixtures, polysiloxanes, polyethers, polyesters, urethane-acryl copolymers, cellulose acetate propionate, siloxane-urethane copolymers, polyurethane-polymethacryl mixtures, silicone-acryl copolymers, vinyl acetate polymers, and mixtures thereof. Exemplary secondary film forming resins usable in the formulations of the present invention include, for example, toluene sulfonamide/epoxy resins, e.g. tosylamide and non-drying alkyd resins, acrylic polymers and copolymers, polyurethane, polyacryls, polymethacryls, cellulosic polymers, styrene-acryl copolymers, polystyrene-polyacryl mixtures, polysiloxanes, polyethers, polyesters, cellulose acetate propionate, urethane-acryl copolymers, siloxane-urethane copolymers, polyurethane-polymethacryl mixtures, silicone-acryl copolymers, vinyl acetate polymers, and mixtures thereof. It is also within the scope of the nail enamel compositions of the present invention to include aldehyde condensation products such as arylsulfonamide formaldehyde resins, specifically toluene sulfonamide formaldehyde resin which is a condensation product of formaldehyde and toluene sulfonamide. These secondary film forming resins are added to the nail enamel compositions of the present invention to strengthen and add acceptable wear characteristics to the primary film forming polymer. In general, the amount of secondary film forming resin ranges form about 2 to 20 percent by weight of the composition, and preferably, about 5 to 12 percent of the composition.

Nitrocellulose is a primary film-forming component in some formulation embodiments of the present invention. A use of low levels of nitrocellulose tends to result in the coated films being easily damaged. On the other hand, a use of high levels of nitrocellulose results in the coated film being too hard and inflexible, resulting in undesirable peeling and hence poor wear resistance.

Other satisfactory film-forming components include cellulose acetate, cellulose acetate butyrate, cellulose acetate propionate, vinyl polymers, polyurethanes, and mixtures of polyurethanes with cellulose acetate butyrate or with nitrocellulose as well as methacrylate and acrylate type polymers. The film-forming component is present in an amount sufficient to provide a stable film upon the nail following the application of the nail enamel to the nail. In general, amounts of the film-forming component of about 8 to about 40 weight percent for some embodiments, and about 10 to about 15 weight percent for other embodiments, are satisfactory. Examples of nitrocellulose are the so called nitrocellulose RS ⅛ sec., RS ¼ sec., and nitrocellulose ½ sec. and nitrocellulose RS 5–6 sec. and 60–80 sec., which have higher viscosities than the earlier grades. The term "RS" refers to the brand of nitrocellulose with a nitrogen content of about 11.2 to 12.8 percent with solubility in esters, ketones, and glycol ethers manufactured by GreenTree Technologies, previously known as Hercules, Inc. The terms ⅛ sec., ½ sec, 5–6 sec, and so forth represent viscosity and refer to the time it takes for a ball to fall a given depth in the material. Nitrocellulose is typically supplied in 70% concentrations, wet with 30% ethyl or isopropyl alcohol. As used in the present invention, the percentage of nitrocellulose in a given composition is on a dry basis.

In one embodiment, the resins include Shin-Etsu KP-543 (acrylic-silicone resin), Uniplex 670P (polyester resin), PCI Group Inc. Lacq-Hard LH-75 (polyamide resin).

Suitable plasticizers are incorporated in the formulation to provide flexibility while exhibiting the wear and chip resistance and shelf stability needed for the composition. Without intending to be limited by theory, it is believed that plasticizers cause a composition to become more easily deformed. Typically, plasticizers are needed in the compositions of the present invention. The compositions of the present invention may comprise from 0% to about 15%, for some embodiments, from 0% to about 10%, and in some embodiments, from about 0% to about 7%, by weight of the composition, of a plasticizer. One or more plasticizers are optionally added to the present compositions.

In one embodiment, the plasticizers include camphor, castor oil, Unitex Chemical Corporation Uniplex 108 (N-ethyl-o/p-Toluenesulfonamide), Uniplex 125A (di-(2-ethylhexyl) adipate), Uniplex 165 (diisobutyl Adipate), Uniplex 260 (Glyceryl Tribenzoate), Uniplex 552 (Pentaerytritrol tetrabenzoate), Phoenix Chemical Inc. Pelemol DIA (diisopropyl adipate), Pelemol TMEB-35 (Trimethylolethane Tribenzoate), Pelemol PTB-35 (Pentaerythyl Tetrabenzoate), Pelemol GTO (Glyceryl Trioctanoate), Alzo International Dermol DPG-2B (Dipropylene glycol dibenzoate), Dermol B-246 (Benzyl Laurate Myristate/Palmitate), Eastman Chemical Corporation TXIB (2,2,4-trimethyl-1,3-pentanediol diisobutyrate), SAIB (Sucrose acetate isobutyrate), Ferro Santicizer 160 (Butyl Benzyl Phthalate), Velsicol Chemical Corporation Benzoflex 284 (Propylene glycol dibenzoate, Dipropylene glycol dibenzoate, propylene glycol monobenzoate) Benzoflex 354 (2,2,4-trimethyl-1,3-pentanediol dibenzoate), Velate 368 (2-ethylhexyl benzoate), CasChem DIPA (diisopropyl adipate).

For some embodiments, plasticizers include Unitex Chemical Corporation Uniplex PX5-115 (N-Alkyl Toluenesulfonamide), Phoenix Chemical Inc. Pelemol B66 (Benzyl Benzoate), Eastman Chemical Corporation Triacetin (Glyceryl triacetate), Uniplex 82 Acetyl Tributyl Citrate.

The nail enamel compositions of the present invention include one or more solvents such as those generally used in conventional nail enamel compositions. Examples of these solvents include ethyl acetate, methyl acetate, n-butyl acetate, iso-butyl acetate, propyl acetate, iso-propyl acetate, amyl acetate, ethanol, isopropanol, n-amyl alcohol, n-butyl alcohol, iso-butanol, cellosolve, butyl cellosolve acetate, cellosolve acetate, methyl cellosolve acetate, butyl cellosolve, ethyl cellosolve, n-butanol, xylene, aromatic (containing phenyl groups), ethers, ketones for example acetone, methyl ethyl ketone, alkanes for example, pentane, cyclopentane, hexane, heptane, cyclohexane, cyclic ethers for example, tetrahydrofuran and 1,4-dioxane, phenylated solvents for example, xylene, chlorinated hydrocarbons for example, methylene chloride, chloroform, glycol ethers, N-methyl pyrrolidone alkyl lactate, and methylchloroform. It is also contemplated that toluene, if desired, can be included as a solvent or diluent for use in a nail enamel composition in accordance with the compositions of the present invention.

The aforementioned solvents can be used alone or in mixtures thereof. In general, the amount of solvent used in the compositions of the present invention range from about 53 to 82% by weight, and, for some embodiments about 65 to 75% by weight. For some embodiments, organic solvents are selected from alcohols and esters having between one and about twenty-five carbon atoms. For some embodiments, alcohols are monohydric. It is also contemplated that, if desired, monohydric alcohols are selected from ethanol, iso-propanol, and n-propanol. For some embodiments, esters are selected from ethyl acetate and butyl acetate. For other embodiments, it is contemplated that polyhydric alcohols are usable.

The following are examples and Laboratory test results of enamels made according to the invention. These examples and test results are presented in order to illustrate features of particular embodiments of the present invention and are not intended to limit the scope of the present invention.

TABLE 1

| Clear Topcoat Ingredient | 1A Weight percent | 1B Weight percent | 1C Weight percent |
| --- | --- | --- | --- |
| Ethyl Acetate | 40.00 | 40.00 | 40.00 |
| Butyl Acetate | 21.00 | 21.00 | 21.00 |
| Nitrocellulose (dry) | 14.00 | 14.00 | 14.00 |
| Isopropyl alcohol | 6.00 | 6.00 | 6.00 |
| Polyester resin (75% solids) | 12.00 | 12.00 | 12.00 |
| Dibutyl phthalate | 7.00 | — | — |
| Butylphthalimide Isopropylphthalimide | — | 7.00 | — |
| Acetyl tributylcitrate | — | — | 7.00 |

The clear topcoat 1B is a topcoat formulation of the present invention, having a butylphthalimide isopropylphthalimide, BIP, concentration of 7.00 percent by weight. The clear topcoat 1A is a control, having a dibutyl phthalate component. The clear topcoat 1 C is a control, having an acetyl tributylcitrate component.

Comparative mechanical film properties of Example 1 of the present invention were measured using a hardness test, adhesion test, and flexibility test as described herein.

Hardness: Using the Erichsen Pendulum Damping Tester Model 299/300 according to Persoz. (NFT 30-016). A standard 6.0 mils wet film thickness (W.F.T) Bird film applicator (MCD Industries) was used to apply films onto (4 ins×6 ins) clean glass plates. The tests were conducted on the films after air-drying at ambient temperature for the specified times below.

TABLE 2

| Time interval after initial application | Average # oscillations | | |
| --- | --- | --- | --- |
| | 1A | 1B | 1C |
| 2 Hrs | 23 | 26 | 26 |
| 24 Hrs. | 50 | 53 | 58 |
| 48 Hrs. | 66 | 73 | 75 |
| 72 Hrs. | 75 | 77 | 81 |
| 96 Hrs. | 76 | 74 | 80 |
| 168 Hrs. | 94 | 96 | 98 |

Adhesion: Using Cross-Cut Tape Test to meet the standards of ASTM Test Method D-3359 on 6.0 mils (W.F.T) applied to (4 ins×6 ins) clean glass panels. A standard 6.0 mils (W.F.T) Bird film applicator (MCD Industries) was used to apply films onto (4 ins×6 ins) clean glass plates. The tests were conducted on the films after air-drying at ambient temperature for the specified times below.

Ratings of adhesion test results according to the classification: 5=Best; 1=worst

TABLE 3

| Time interval after initial application | 1A | 1B | 1C |
| --- | --- | --- | --- |
| 24 Hrs. | 5B | 5B | 5B |
| 48 Hrs. | 5B | 5B | 5B |
| 72 Hrs. | 5B | 5B | 5B |
| 96 Hrs. | 5B | 5B | 5B |
| 168 Hrs. | 5B | 5B | 5B |

Flexibility: According to standards of ASTM Test Method D-522 and D 1737. A standard 6.0 mils (W.F.T) Bird film applicator (MCD Industries) was used to apply films onto clean aluminum panels (6 ins×4 ins Mill Finish 3105 H24 supplied by Q-panel Lab Products, Cleveland, Ohio). Coated panels were uniformly bent using the BYK-Gardner Cylindrical Mandrel. The tests were conducted on the films after air-drying at ambient temperature for the specified times below.

TABLE 4

| Time interval after initial application | 1A | 1B | 1C |
| --- | --- | --- | --- |
| 24 Hrs. | Good | Good | Good |
| 48 Hrs. | Good | Good | Good |
| 72 Hrs. | Good | Good | Good |
| 96 Hrs. | Good | Good | Good |
| 168 Hrs. | Good | Good | Good |

The mechanical tests illustrated that the topcoat formulation performance of the formulation of the present invention was at least as good, when measured in terms of hardness, adhesion, and flexibility, as the performance of the topcoat free of BIP and containing dibutyl phthalate and the topcoat free of BIP and containing acetyl tributylcitrate. The topcoat formulation of the present invention did not produce any adverse effects in users.

The following are examples of compositions of colored nail enamel that demonstrate embodiments under the scope of the present invention. There are other possible variations that are within the scope and hence these examples are not to be construed as limitations.

TABLE 5

| Ingredient | EXAMPLE 2 Red crème shade nail enamel Weight percent | EXAMPLE 3 Mauve pearl shade nail enamel Weight percent |
|---|---|---|
| Ethyl Acetate | 38.410 | 37.950 |
| Butyl Acetate | 25.600 | 25.300 |
| Nitrocellulose (dry) | 12.010 | 11.860 |
| Isopropyl alcohol | 5.381 | 5.080 |
| Tosylamide/epoxy resin | 8.532 | 9.080 |
| *Butylphthalimide Isopropylphthalimide | 7.498 | 6.850 |
| Stearalkonium Hectorite | 0.960 | 1.036 |
| Phosphoric acid | 0.017 | 0.018 |
| Benzophenone-1 | 0.175 | 0.188 |
| Iron Oxide Red | 0.100 | — |
| Iron Oxide black | 0.050 | — |
| D&C Red No. 7 Calcium Lake | 0.539 | — |
| FD&C Yellow#5 Aluminum Lake | 0.234 | — |
| Titanium Dioxide | 0.324 | 0.515 |
| Dimethicone | 0.170 | 0.176 |
| Bismuth Oxychloride | — | 0.400 |
| Mica | — | 1.387 |
| D&C Red No. 34 | — | 0.160 |

Presented below is a summary of performance of specified plasticizers when used with BIP. The BIP concentration used was between 6.80 and 7.50 percent by weight. The first table shows adhesion and hardness in a red creme shade of nail enamel, made with polyester resin B75. The Pelemol GTO formulation displayed a comparatively high hardness to the BIP formulation but a lower adhesion. The BIP in each of polyester resin B75 and tosylamide/epoxy resin E75 displayed slight cracking at 168 hours. The Triacetin and BIP, Dermol DPG-2B and BIP, Pelemol DIA and BIP, and Santicizer 160 and BIP formulations displayed an adhesion that dropped off over time and a hardness that was comparatively low up to about 48 hours, but became greater over time. These formulations did not perform as well as the BIP formulation. The GTB and BIP, TXIB and BIP, and BB and BIP formulations displayed strong adhesion and hardness over the period of the test. A similar performance was observed when a Tosylamide/Epoxy Resin E75 was substituted for the Polyester Resin B75. These formulations displayed cracking within 24 to 48 hours.

In another test, plasticizer performance was measured in conjunction with BIP in a 75/25 weight ratio and Polyester Resin B75. The performance of the plasticizer with BIP in a 75/25 ratio was comparable to performance, as measured by adhesion and hardness, of formulations of plasticizers and full strength BIP. The performance of plasticizers in a formulation with BIP in a 75/25 ratio and Tosylamide/Epoxy Resin E75 was, in some instances, weaker than for full strength BIP formulations or the formulation with BIP 75/25 and Polyester Resin B75. The Pelemol GTO displayed a very low adhesion. Plasticizers that cracked within 24 to 48 hours included Uniplex 365, Pelemol GTO, Uniplex 165A, and Benzoflex 284.

In one other test, plasticizers GTB, TXIB, BB and SAIB were measured in a formulation that included BIP in a 50/50 ratio and Polyester Resin B75 and with BIP in a 50/50 ratio and Tosylamide Resin E75. The hardness and adhesion of enamels made with these formulations was substantially the same as formulations made with full strength BIP. Each of these formulations displayed cracking within 24 to 48 hours. Testing of the nail enamel was performed over a period of seven days. It is believed that the nail enamel formulations that include BIP remain substantially free of cracks for at least about 10 days.

TABLE 6

| | Plasticizer and Polyester Resin B75 | | | | | | | | | | |
|---|---|---|---|---|---|---|---|---|---|---|---|
| | ADHESION | | | | | HARDNESS | | | | | |
| Red crème shade | 24 h | 48 h | 72 h | 144 h | 168 h | 2 h | 24 h | 48 h | 72 h | 144 h | 168 h |
| BIP | 5 | 5 | 4 | 4 | 4 | 34 | 85 | 99 | 120 | 124 | 145 |
| Dermol DPG-2B | 5 | 3 | 3 | 3 | 2 | 41 | 97 | 107 | 129 | 145 | 142 |
| Pelemol DIA | 5 | 4 | 2 | 2 | 2 | 56 | 117 | 135 | 177 | 210 | 207 |
| Santicizer 160 | 5 | 4 | 3 | 2 | 2 | 36 | 105 | 109 | 140 | 161 | 155 |
| GTB | 4 | 4 | 4 | 4 | 4 | 46 | 107 | 118 | 127 | 147 | 149 |
| TXIB | 4 | 4 | 4 | 4 | 4 | 70 | 149 | 164 | 166 | 187 | 184 |
| BB | 5 | 5 | 4 | 4 | 4 | 62 | 138 | 149 | 157 | 171 | 173 |
| SAIB | 3 | 2 | 2 | 2 | 2 | 64 | 159 | 159 | 168 | 213 | 226 |
| Triacetin | 5 | 5 | 5 | 4 | 3 | 37 | 75 | 87 | 109 | 137 | 141 |
| Uniplex 365 | 5 | 5 | 4 | 4 | 3 | 68 | 106 | 108 | 124 | 143 | 141 |
| Pelemol GTO | 1 | 1 | 1 | 1 | 1 | 76 | 153 | 188 | 206 | 220 | 209 |
| Uniplex 165A | 3 | 3 | 2 | 2 | 2 | 98 | 150 | 162 | 168 | 185 | 173 |
| Benzoflex 284 | 5 | 4 | 4 | 3 | 2 | 45 | 94 | 116 | 121 | 155 | 139 |
| Acetyl tributyl citrate | 5 | 4 | 4 | 4 | 3 | 48 | 121 | 133 | 155 | 163 | 165 |
| Dibutyl phthalate | 5 | 4 | 4 | 3 | 3 | 58 | 117 | 128 | 157 | 154 | 167 |

TABLE 7

Plasticizers and Tosylamide/Epoxy Resin E75

| Red crème shade | ADHESION | | | | | HARDNESS | | | | | |
|---|---|---|---|---|---|---|---|---|---|---|---|
| | 24 h | 48 h | 72 h | 144 h | 168 h | 2 h | 24 h | 48 h | 72 h | 144 h | 168 h |
| BIP | 5 | 5 | 4 | 4 | 4 | 31 | 82 | 101 | 102 | 116 | 127 |
| Dermol DPG-2B | 5 | 5 | 5 | 5 | 5 | 38 | 97 | 106 | 128 | 141 | 142 |
| Pelemol DIA | 5 | 4 | 4 | 4 | 3 | 53 | 128 | 145 | 184 | 210 | 205 |
| Santicizer 160 | 5 | 4 | 3 | 3 | 3 | 37 | 103 | 107 | 130 | 147 | 145 |
| GTB | 5 | 5 | 4 | 3 | 3 | 41 | 95 | 116 | 121 | 137 | 142 |
| TXIB | 4 | 4 | 4 | 3 | 3 | 58 | 128 | 148 | 151 | 176 | 172 |
| BB | 5 | 5 | 5 | 4 | 4 | 51 | 120 | 138 | 144 | 176 | 160 |
| SAIB | 3 | 3 | 2 | 2 | 2 | 57 | 149 | 171 | 182 | 176 | 213 |
| Triacetin | 5 | 5 | 5 | 4 | 4 | 34 | 71 | 94 | 92 | 141 | 137 |
| Uniplex 365 | 5 | 5 | 4 | 3 | 3 | 58 | 107 | 118 | 126 | 142 | 141 |
| Pelemol GTO | 5 | 5 | 5 | 4 | 4 | 71 | 161 | 191 | 200 | 210 | 209 |
| Uniplex 165A | 3 | 2 | 2 | 2 | 2 | 88 | 140 | 164 | 174 | 184 | 181 |
| Benzoflex 284 | 5 | 4 | 4 | 3 | 3 | 37 | 86 | 108 | 124 | 149 | 146 |
| Acetyl tributyl citrate | 5 | 5 | 5 | 5 | 4 | 33 | 110 | 128 | 146 | 152 | 155 |
| Dibutyl phthalate | 5 | 5 | 5 | 5 | 4 | 40 | 123 | 138 | 148 | 153 | 159 |

TABLE 8

| Red crème shade | ADHESION | | | | | HARDNESS | | | | | |
|---|---|---|---|---|---|---|---|---|---|---|---|
| | 24 h | 48 h | 72 h | 144 h | 168 h | 2 h | 24 h | 48 h | 72 h | 144 h | 168 h |
| Plasticizer/BIP in a 75/25 ratio and Polyester Resin B75 | | | | | | | | | | | |
| Dermol DPG-2B | 5 | 5 | 5 | 5 | 5 | 35 | 87 | 126 | 128 | 130 | 137 |
| Pelemol DIA | 3 | 2 | 2 | 2 | 2 | 44 | 116 | 147 | 154 | 165 | 155 |
| Santicizer 160 | 5 | 5 | 5 | 5 | 5 | 37 | 98 | 131 | 144 | 155 | 148 |
| Triacetin | 5 | 5 | 5 | 5 | 5 | 37 | 86 | 93 | 119 | 133 | 133 |
| Uniplex 365 | 5 | 5 | 5 | 5 | 5 | 61 | 136 | 140 | 147 | 162 | 168 |
| Pelemol GTO | 3 | 3 | 2 | 2 | 1 | 61 | 116 | 123 | 132 | 156 | 183 |
| Uniplex 165A | 5 | 5 | 5 | 5 | 5 | 83 | 151 | 168 | 175 | 180 | 186 |
| Benzoflex 284 | 5 | 5 | 5 | 5 | 5 | 43 | 98 | 112 | 113 | 144 | 143 |
| Plasticizer/BIP in a 75/25 ratio and Tosylamide Resin E75 | | | | | | | | | | | |
| Dermol DPG-2B | 5 | 4 | 3 | 3 | 3 | 41 | 89 | 123 | 136 | 141 | 135 |
| Pelemol DIA | 5 | 4 | 4 | 3 | 3 | 36 | 103 | 147 | 160 | 169 | 164 |
| Santicizer 160 | 5 | 4 | 4 | 3 | 3 | 37 | 92 | 125 | 143 | 143 | 134 |
| Triacetin | 5 | 5 | 2 | 2 | 2 | 33 | 75 | 80 | 108 | 131 | 121 |
| Uniplex 365 | 5 | 5 | 3 | 2 | 2 | 47 | 170 | 114 | 148 | 160 | 151 |
| Pelemol GTO | 0 | 0 | 0 | 0 | 0 | 54 | 100 | 103 | 110 | 130 | 128 |
| Uniplex 165A | 4 | 4 | 2 | 2 | 2 | 58 | 156 | 142 | 175 | 182 | 190 |
| Benzoflex 284 | 4 | 4 | 3 | 2 | 2 | 35 | 88 | 95 | 126 | 141 | 140 |

TABLE 9

| Red crème shade | ADHESION | | | | | HARDNESS | | | | | |
|---|---|---|---|---|---|---|---|---|---|---|---|
| | 24 h | 48 h | 72 h | 144 h | 168 h | 2 h | 24 h | 48 h | 72 h | 144 h | 168 h |
| Plasticizer/BIP in a 50/50 Ratio and Polyester Resin B75 | | | | | | | | | | | |
| GTB | 5 | 5 | 5 | 4 | 4 | 30 | 85 | 109 | 109 | 120 | 158 |
| TXIB | 5 | 5 | 4 | 4 | 4 | 37 | 97 | 118 | 121 | 119 | 131 |
| BB | 5 | 5 | 4 | 4 | 3 | 37 | 96 | 115 | 119 | 126 | 143 |
| SAIB | 5 | 5 | 3 | 3 | 3 | 34 | 105 | 118 | 139 | 165 | 167 |
| Plasticizer/BIP in a 50/50 Ratio and Tosylamide/Epoxy Resin E75 | | | | | | | | | | | |
| GTB | 5 | 5 | 5 | 5 | 5 | 32 | 88 | 109 | 138 | 119 | 139 |
| TXIB | 5 | 5 | 5 | 5 | 4 | 36 | 94 | 118 | 128 | 135 | 143 |
| BB | 5 | 5 | 5 | 5 | 5 | 33 | 89 | 116 | 129 | 135 | 145 |
| SAIB | 5 | 5 | 5 | 5 | 5 | 36 | 103 | 138 | 148 | 166 | 174 |

The results for use of BIP to make a Pearl shade nail enamel are shown below. The BIP showed very good values for adhesion and hardness when used with all of the resins tested. The BIP performance was better than Uniplex when used with Polyester Resin B75. The BIP performance was better than Triacetin when used with Tosylamide Epoxy Resin E75. A formulation of BIP in a 75/25 ratio and Polyester Resin B75 displayed a performance better than Pelemol GTO and Dermol DPG-2B, when used as the sole plasticizer. A 50/50 ratio of BIP with Polyester Resin B75 in one embodiment, and Tosylamide Epoxy Resin E75, in another embodiment, displayed results comparable to adhesion and hardness results shown with GTB, TXIB, BB and SAIB.

TABLE 10

| Pearl shade | ADHESION | | | | | HARDNESS | | | | | |
|---|---|---|---|---|---|---|---|---|---|---|---|
| | 24 h | 48 h | 72 h | 144 h | 168 h | 2 h | 24 h | 48 h | 72 h | 144 h | 168 h |
| Plasticizers and Polyester Resin B75 | | | | | | | | | | | |
| BIP | 5 | 5 | 5 | 5 | 5 | 37 | 82 | 118 | 120 | 138 | 146 |
| GTB | 5 | 5 | 5 | 5 | 5 | 43 | 104 | 102 | 128 | 144 | 143 |
| TXIB | 4 | 4 | 3 | 3 | 3 | 74 | 130 | 143 | 154 | 193 | 183 |
| BB | 5 | 5 | 5 | 5 | 5 | 64 | 140 | 157 | 154 | 175 | 168 |
| SAIB | 4 | 4 | 4 | 4 | 4 | 69 | 162 | 179 | 168 | 204 | 210 |
| Dermol DPG-2B | 5 | 4 | 3 | 3 | 2 | 33 | 86 | 86 | 118 | 143 | 137 |
| Pelemol DIA | 5 | 4 | 3 | 3 | 2 | 40 | 112 | 111 | 153 | 186 | 176 |
| Santicizer 160 | 5 | 4 | 3 | 3 | 2 | 45 | 114 | 125 | 132 | 156 | 166 |
| Triacetin | 5 | 5 | 5 | 5 | 5 | 35 | 83 | 108 | 122 | 147 | 143 |
| Uniplex 365 | 5 | 5 | 5 | 5 | 5 | 66 | 128 | 160 | 149 | 157 | 168 |
| Pelemol GTO | 5 | 5 | 5 | 4 | 4 | 74 | 148 | 200 | 213 | 200 | 219 |
| Uniplex 165A | 2 | 2 | 2 | 2 | 2 | 88 | 143 | 154 | 148 | 176 | 159 |
| Benzoflex 284 | 5 | 5 | 5 | 5 | 5 | 34 | 83 | 101 | 133 | 154 | 155 |
| Acetyl tributyl citrate | 5 | 5 | 5 | 5 | 5 | 42 | 108 | 129 | 154 | 159 | 160 |
| Dibutyl phthalate | 5 | 5 | 5 | 5 | 5 | 48 | 120 | 131 | 159 | 159 | 158 |
| Plasticizers and Tosylamide/Epoxy Resin E75 | | | | | | | | | | | |
| BIP | 5 | 5 | 5 | 5 | 5 | 27 | 78 | 101 | 112 | 129 | 134 |
| GTB | 5 | 5 | 5 | 5 | 5 | 32 | 98 | 116 | 118 | 113 | 146 |
| TXIB | 5 | 4 | 4 | 4 | 4 | 52 | 130 | 139 | 145 | 170 | 178 |
| BB | 5 | 5 | 5 | 5 | 5 | 48 | 117 | 138 | 141 | 160 | 168 |
| SAIB | 5 | 4 | 4 | 4 | 4 | 56 | 154 | 177 | 173 | 217 | 202 |
| Dermol DPG-2B | 5 | 5 | 5 | 4 | 4 | 32 | 74 | 86 | 119 | 134 | 138 |
| Pelemol DIA | 5 | 4 | 3 | 3 | 3 | 42 | 120 | 169 | | 176 | 162 |
| Santicizer 160 | 5 | 4 | 4 | 4 | 3 | 44 | 117 | 130 | 153 | 163 | 171 |
| Triacetin | 2 | 2 | 2 | 2 | 2 | 29 | 73 | 92 | 113 | 149 | 143 |
| Uniplex 365 | 2 | 2 | 2 | 2 | 2 | 53 | 123 | 132 | 147 | 169 | 168 |
| Pelemol GTO | 5 | 5 | 5 | 4 | 4 | 74 | 148 | 200 | 213 | 200 | 209 |
| Uniplex 165A | 5 | 5 | 4 | 3 | 3 | 89 | 183 | 189 | 189 | 192 | 202 |
| Benzoflex 284 | 5 | 5 | 5 | 5 | 5 | 34 | 83 | 101 | 133 | 154 | 155 |
| Acetyl tributyl citrate | 5 | 5 | 5 | 5 | 5 | 33 | 110 | 128 | 146 | 152 | 155 |
| Dibutyl phthalate | 5 | 5 | 5 | 5 | 4 | 40 | 123 | 138 | 148 | 153 | 159 |

TABLE 11

| Pearl shade | | | | | | | | | | | |
|---|---|---|---|---|---|---|---|---|---|---|---|
| Plasticizer/BIP in a 75/25 Ratio with Polyester Resin B75 | | | | | | | | | | | |
| Dermol DPG-2B | 5 | 4 | 3 | 2 | 3 | 31 | 75 | 109 | 115 | 127 | 124 |
| Pelemol DIA | 5 | 4 | 2 | 3 | 2 | 40 | 107 | 128 | 151 | 151 | 142 |
| Santicizer 160 | 5 | 4 | 4 | 4 | 3 | 40 | 91 | 124 | 148 | 148 | 145 |
| Triacetin | 5 | 5 | 5 | 5 | 5 | 37 | 86 | 93 | 119 | 133 | 133 |
| Uniplex 365 | 5 | 5 | 5 | 5 | 5 | 61 | 136 | 140 | 147 | 162 | 168 |
| Pelemol GTO | 3 | 3 | 2 | 2 | 1 | 61 | 116 | 123 | 132 | 156 | 183 |
| Uniplex 165A | 5 | 5 | 5 | 5 | 5 | 83 | 151 | 168 | 175 | 180 | 186 |
| Benzoflex 284 | 5 | 5 | 5 | 5 | 5 | 43 | 98 | 112 | 113 | 144 | 143 |
| Plasticizer/BIP in a 75/25 Ratio with Tosylamide/Epoxy Resin E75 | | | | | | | | | | | |
| Dermol DPG-2B | 5 | 5 | 4 | 4 | 3 | 30 | 69 | 110 | 123 | 131 | 120 |
| Pelemol DIA | 5 | 4 | 4 | 3 | 4 | 34 | 106 | 145 | 153 | 160 | 146 |
| Santicizer 160 | 5 | 5 | 5 | 5 | 5 | 35 | 91 | 128 | 139 | 146 | 140 |
| Triacetin | 5 | 5 | 5 | 5 | 5 | 31 | 79 | 83 | 132 | 156 | 153 |
| Uniplex 365 | 5 | 5 | 5 | 5 | 5 | 49 | 115 | 127 | 155 | 160 | 163 |
| Pelemol GTO | 5 | 5 | 5 | 5 | 5 | 52 | 126 | 139 | 137 | 192 | 190 |
| Uniplex 165A | 5 | 5 | 5 | 5 | 4.5 | 65 | 150 | 168 | 180 | 186 | 193 |
| Benzoflex 284 | 5 | 5 | 5 | 5 | 5 | 33 | 87 | 94 | 122 | 140 | 139 |
| Plasticizer/BIP in a 50/50 Ratio with Polyester Resin B75 | | | | | | | | | | | |
| GTB | 5 | 5 | 5 | 4 | 3 | 41 | 100 | 122 | 121 | 133 | 158 |
| TXIB | 5 | 5 | 4 | 4 | 4 | 37 | 97 | 118 | 121 | 119 | 131 |
| BB | 5 | 5 | 4 | 4 | 3 | 37 | 96 | 115 | 119 | 126 | 143 |
| SAIB | 5 | 5 | 3 | 3 | 3 | 34 | 105 | 118 | 139 | 165 | 167 |

TABLE 11-continued

Pearl shade

| Plasticizer/BIP in a 50/50 Ratio with Tosylamide Epoxy Resin E75 | | | | | | | | | | | |
|---|---|---|---|---|---|---|---|---|---|---|---|
| GTB | 5 | 5 | 5 | 5 | 5 | 37 | 86 | 114 | 128 | 140 | 153 |
| TXIB | 5 | 5 | 5 | 5 | 5 | 39 | 101 | 128 | 152 | 155 | 156 |
| BB | 5 | 5 | 5 | 5 | 5 | 43 | 102 | 118 | 129 | 153 | 139 |
| SAIB | 5 | 5 | 5 | 4 | 4 | 45 | 114 | 134 | 139 | 158 | 167 |

Additional examples using Pelemol BIP in combination with Glyceryl Triacetate

TABLE 12

| Red Crème shade | FORMULA EC | FORMULA FC | FORMULA GC | FORMULA HC[1] | FORMULA IC[2] |
|---|---|---|---|---|---|
| Ethyl Acetate | 41.271 | 41.238 | 41.386 | 41.262 | 41.262 |
| Butyl Acetate | 22.234 | 22.200 | 22.282 | 22.218 | 22.218 |
| Nitrocellulose (dry) ¼ sec R.S | 9.603 | 9.603 | 6.005 | 9.603 | 9.603 |
| ½ sec R.S | 2.407 | 2.407 | 6.005 | 2.407 | 2.407 |
| Isopropyl alcohol | 5.380 | 5.380 | 5.150 | 5.15 | 5.15 |
| Tosylamide/epoxy resin | 8.532 | 7.644 | 7.644 | 7.644 | 8.880 |
| Butylphthalimide isopropylphthalimide | 7.498 | 7.498 | 7.498 | 2.983 | 4.488 |
| Acrylic- silicone copolymer | 0.000 | 0.955 | 0.955 | 0.955 | 0.955 |
| Glyceryl Triacetate | 0.000 | 0.000 | 0.000 | 4.516 | 3.010 |
| Stearalkonium Hectorite | 0.960 | 0.960 | 0.960 | 0.960 | 0.960 |
| Benzophenone-1 | 0.175 | 0.175 | 0.175 | 0.175 | 0.175 |
| Iron Oxides | 0.153 | 0.153 | 0.153 | 0.153 | 0.153 |
| Phosphoric acid | 0.017 | 0.017 | 0.017 | 0.017 | 0.017 |
| D&C Red No.6 | 0.673 | 0.673 | 0.673 | 0.673 | 0.673 |
| D&C Red No. 7 Calcium Lake | 0.539 | 0.539 | 0.539 | 0.539 | 0.539 |
| Titanium Dioxide | 0.324 | 0.324 | 0.324 | 0.324 | 0.324 |
| FD&C Yellow No. 5 Aluminum Lake | 0.234 | 0.234 | 0.234 | 0.234 | 0.234 | ratios of BIP/ Glyceryl Triacetate
C = crème shade
P = Pearl shade
[1]Formula HC: Ratio of BIP/GTA - 40/60
[2]Formula IC: Ratio BIP/GTA- 60/40
[3]Formula HP: Ratio of BIP/GTA 30/70
[4]Formula IP: Ratio of BIP/GTA 50/50

TABLE 13

| | Red Crème shade | | | | |
|---|---|---|---|---|---|
| TEST RESULTS | FORMULA EC | FORMULA FC | FORMULA GC | FORMULA HC | FORMULA IC |
| Hardness: | | | | | |
| 2 Hrs. | 25 | 26 | 24 | 22 | 23 |
| 24 Hrs. | 60 | 65 | 61 | 55 | 53 |
| 48 Hrs. | 72 | 80 | 77 | 63 | 67 |
| 72 Hrs. | 83 | 91 | 88 | 70 | 74 |
| 144 Hrs. | 119 | 119 | 119 | 96 | 101 |
| 168 Hrs. | 122 | 139 | 136 | 119 | 122 |
| Adhesion: | | | | | |
| 24 Hrs. | 5 | 5 | 5 | 5 | 5 |
| 48 Hrs. | 5 | 5 | 5 | 5 | 5 |
| 72 Hrs. | 5 | 5 | 5 | 5 | 5 |
| 144 Hrs. | 4 | 5 | 5 | 5 | 5 |
| 168 Hrs. | 4 | 5 | 5 | 5 | 5 |
| Flexibility: | | | | | |
| 24 Hrs. | Ok | Ok | Ok | Ok | Ok |
| 48 Hrs. | Ok | Ok | Ok | Ok | Ok |
| 72 Hrs. | Ok | Cracked | Ok | Ok | Ok |

TABLE 13-continued

| | Red Crème shade | | | | |
|---|---|---|---|---|---|
| TEST RESULTS | FORMULA EC | FORMULA FC | FORMULA GC | FORMULA HC | FORMULA IC |
| 144 Hrs. | Stretched | Cracked | Ok | Ok | Ok |
| 168 Hrs. | Cracked | Cracked | Cracked | Cracked | Cracked | ratios of BIP/ Glyceryl Triacetate
C = crème shade
P = Pearl shade
[1]Formula HC: Ratio of BIP/GTA - 40/60
[2]Formula IC: Ratio BIP/GTA- 60/40
[3]Formula HP: Ratio of BIP/GTA 30/70
[4]Formula IP: Ratio of BIP/GTA 50/50

TABLE 14

| Pearl shade | FORMULA EP | FORMULA FP | FORMULA GP | FORMULA HP[3] | FORMULA IP[4] |
|---|---|---|---|---|---|
| Ethyl Acetate | 40.581 | 40.576 | 40.576 | 40.576 | 40.576 |
| Butyl Acetate | 21.853 | 21.849 | 21.849 | 21.849 | 21.849 |
| Nitrocellulose (dry) ¼ sec R.S | 11.858 | 11.858 | 5.929 | 11.858 | 11.858 |
| ½ sec R.S | | | 5.929 | | |
| Isopropyl alcohol | 5.082 | 5.082 | 5.082 | 5.082 | 5.082 |
| Tosylamide/epoxy resin (solids) | 9.081 | 8.081 | 8.081 | 8.081 | 8.081 |
| Butylphthalimide isopropylphthalimide | 6.854 | 6.854 | 6.854 | 2.081 | 3.427 |
| Acrylic- silicone copolymer solids) | 0.000 | 1.009 | 1.009 | 1.009 | 1.009 |
| Glyceryl Triacetate | 0.000 | 0.000 | 0.000 | 4.772 | 3.427 |
| Stearalkonium Hectorite | 1.036 | 1.036 | 1.036 | 1.036 | 1.036 |
| Bismuth Oxychloride | 0.40 | 0.40 | 0.40 | 0.40 | 0.40 |
| Dimethicone | 0.176 | 0.176 | 0.176 | 0.176 | 0.176 |
| Iron Oxides | 0.811 | 0.811 | 0.811 | 0.811 | 0.811 |
| Benzophenone-1 | 0.188 | 0.188 | 0.188 | 0.188 | 0.188 |
| Phosphoric acid | 0.018 | 0.018 | 0.018 | 0.018 | 0.018 |
| Mica | 1.387 | 1.387 | 1.387 | 1.387 | 1.387 |
| D&C Red No. 34 | 0.160 | 0.160 | 0.160 | 0.160 | 0.160 |
| Titanium Dioxide | 0.515 | 0.515 | 0.515 | 0.515 | 0.515 |

TABLE 15

| | Pearl shade | | | | |
|---|---|---|---|---|---|
| TEST RESULTS | FORMULA EP | FORMULA FP | FORMULA GP | FORMULA HP[3] | FORMULA IP[4] |
| Hardness: | | | | | |
| 2 Hrs. | 21 | 25 | 24 | 21 | 22 |
| 24 Hrs. | 64 | 64 | 63 | 49 | 51 |
| 48 Hrs. | 76 | 84 | 81 | 64 | 68 |
| 72 Hrs. | 99 | 98 | 93 | 74 | 77 |
| 144 Hrs. | 126 | 121 | 126 | 109 | 108 |
| 168 Hrs. | 128 | 140 | 139 | 125 | 126 |
| Adhesion: | | | | | |
| 24 Hrs. | 5 | 5 | 5 | 5 | 5 |
| 48 Hrs. | 5 | 5 | 5 | 5 | 5 |
| 72 Hrs. | 5 | 5 | 5 | 5 | 5 |
| 144 Hrs. | 5 | 5 | 5 | 5 | 5 |
| 168 Hrs. | 5 | 5 | 5 | 5 | 5 |
| Flexibility: | | | | | |
| 24 Hrs. | Ok | Ok | Ok | Ok | Ok |
| 48 Hrs. | Ok | Ok | Ok | Ok | Ok |
| 72 Hrs. | Ok | Ok | Ok | Ok | Ok |
| 144 Hrs. | Stretched | Stretched | Stretched | Ok | Ok |
| 168 Hrs. | Sl. Cracked | Sl. Cracked | Stretched | Ok | Ok |

Testing of the red creme shade and the pearl shade was performed to confirm that BIP formulations are usable in formulations containing a variety of types and concentrations of coloring agents. The red creme formulations displayed lesser adhesion and flexibility than pearl shade formulations. This performance parallels a tendency for the red creme shade to chip more easily in phthalate-based formulations.

The nail enamel embodiments of the present invention are made by blending the BIP into the formulation alone, or, optionally, with other plasticizers. Other ingredients are added in accordance with methods known to those skilled in the art. The nail enamel is dispensed into containers. The containers typically have applicators that are an integral part of the container or that are packaged with the container. One type of applicator is a brush. The enamel is applied to nails as a base coat or a topcoat.

A consumer use study was conducted on the mauve pearl shade. The study included seven test subjects. The two products tested included a formulation that included BIP and that was phthalate-free and a formulation that included phthalates. There was no difference detected between the two products for overall wear and chipping. Gloss and appearance were also comparable, although a preference for the gloss of the BIP containing formula was noted in the laboratory.

Each of any foregoing patents, patent applications and references described herein is incorporated by reference in its entirety. Having described particular embodiments in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

What is claimed is:

1. A method for making a cosmetic film substantially free from phthalates and that has a hardness, adhesion, flexibility, gloss and long shelf life that prevent cracking for at least about 7 days after application to a nail, comprising:

providing one or more primary film forming polymers;

providing one or more secondary film forming resins;

providing butylphthalimide isopropylphthalimide;
   and blending the primary film forming polymer, secondary film forming resin and butylphthalimide isopropylphthalimide without phthalate addition in a weight percent concentration of about 1 to 10 weight percent to make a cosmetic film having a hardness, adhesion, flexibility, gloss and long shelf life.

2. The method of claim 1, further comprising blending the butylphthalimide isopropylphthalimide with another plasticizer.

3. The method of claim 1, further comprising adding color agents to the cosmetic film.

4. A method for coating nails with a cosmetic film, comprising:

providing a cosmetic film comprising butylphthalimide isopropylphthalimide; and applying the cosmetic film to one or more mammalian nail.

5. A colored nail enamel free from phthalates, comprising:

An acetate;

Nitrocellulose;

butylphthalimide isopropylphthalimide;

tosylamide/epoxy resin; and coloring agents.

6. The colored nail enamel of claim 5 wherein the butylphthalimide isopropylphthalimide concentration is within a range of about 1 and 10 percent by weight.

7. The method of claim 4 wherein the coating is applied as a base coat.

8. The method of claim 4 wherein the coating is applied as a topcoat.

9. The method of claim 4 wherein the coating is applied as a color coat.

10. The method of claim 4 wherein the coating is applied as a clear coat.

11. The method of claim 1 wherein the secondary film-forming polymers are selected from the group consisting of polyurethanes, polyacryls, polymethacryls, cellulosic polymers, styrene-acryl copolymers, polystyrene-polyacryl mixtures, polysiloxanes, polyesters, polyethers, cellulose acetate propionate, urethane-acryl copolymers, siloxane-urethane copolymers, vinyl acetate polymers, and mixtures thereof.

12. The method of claim 1 wherein the secondary film forming polymers are selected from a group consisting of acrylic-silicone resin, polyester resin, and polyamide resin.

* * * * *